(12) United States Patent
Choay et al.

(10) Patent No.: US 6,905,458 B2
(45) Date of Patent: Jun. 14, 2005

(54) ECHOGENIC OR RADIO OPAQUE DEVICE FOR REMOVAL FROM OR TRANSFER INTO THE GENITAL ORGANS

(75) Inventors: Patrick Choay, Paris (FR); Patrick Bouveret, Neuilly-en-Thelle (FR)

(73) Assignee: Prodimed, Neuilly-en-Thelle (FR)

( * ) Notice: Subject to any disclaimer, the term of this patent is extended or adjusted under 35 U.S.C. 154(b) by 0 days.

(21) Appl. No.: 09/879,949

(22) Filed: Jun. 14, 2001

(65) Prior Publication Data

US 2002/0032379 A1 Mar. 14, 2002

(30) Foreign Application Priority Data

Jun. 14, 2000 (FR) .............................................. 00 07576

(51) Int. Cl.[7] .............................. A61B 17/43; A61D 7/00
(52) U.S. Cl. .......................... 600/34; 600/33; 604/529
(58) Field of Search .......................... 604/93.01, 128, 604/164.01–164.02, 164.03, 167.01, 167.06, 181, 264, 218, 523, 529; 600/562, 565–567, 573, 33–35

(56) References Cited

U.S. PATENT DOCUMENTS

| | | | | |
|---|---|---|---|---|
| 4,796,637 A | * | 1/1989 | Mascuch et al. ............ | 600/435 |
| 5,327,891 A | * | 7/1994 | Rammler .................... | 600/435 |
| 5,492,130 A | | 2/1996 | Chiou | |
| 5,683,345 A | * | 11/1997 | Waksman et al. ............... | 600/3 |
| 5,728,064 A | * | 3/1998 | Burns et al. ........... | 604/100.01 |
| 5,800,389 A | | 9/1998 | Burney et al. | |
| 5,921,933 A | * | 7/1999 | Sarkis et al. ................. | 600/459 |
| 5,921,978 A | * | 7/1999 | Thompson et al. ......... | 604/529 |
| 6,030,377 A | * | 2/2000 | Linhares et al. ............... | 606/7 |
| 6,511,415 B1 | * | 1/2003 | Christine et al. ............. | 600/35 |
| 6,527,752 B1 | * | 3/2003 | Bosley et al. ............... | 604/264 |
| 6,610,005 B1 | * | 8/2003 | Tao ............................. | 600/34 |

FOREIGN PATENT DOCUMENTS

| | | |
|---|---|---|
| EP | 0 456 342 | 11/1991 |
| FR | 2 635 453 | 2/1990 |
| FR | 2 715 824 | 8/1995 |
| GB | 2 118 840 | 11/1983 |

* cited by examiner

*Primary Examiner*—Nicholas D. Micchesi
*Assistant Examiner*—Catherine S. Williams
(74) *Attorney, Agent, or Firm*—Young & Thompson

(57) ABSTRACT

An echogenic and/or radio-opaque device adapted to permit carrying out removals from the genital organs for analysis, or adapted to promote the transfer of products, particularly gametes or embryos, into the female genital organs, or again adapted to carry out tests for the introduction of catheters into the uterus and to analyze the morphology of the neck of the uterus and of the uterine cavity. The device comprises an echogenic and/or radio-opaque material permitting visualizing by medical imagery, particularly by echography or radiography, the position of the usable orifice or of the distal portion of the device.

3 Claims, 3 Drawing Sheets

ECHOGENIC OR RADIO OPAQUE DEVICE FOR REMOVAL FROM OR TRANSFER INTO THE GENITAL ORGANS

FIELD OF THE INVENTION

The present invention relates to an echogenic and/or radio opaque device adapted to permit carrying out removals from genital organs, such as removal of physiological liquids or fragments from the internal wall of genital organs, or adapted to permit transfer of products, particularly gametes or embryos, into the female genital organs, particularly into the uterus or the anatomical tubes.

BACKGROUND OF THE INVENTION

Removal devices in use at present, generally comprise a cylindrical tube open at its two ends, of an external diameter of about 3 millimeters and an internal diameter of about 1.5 to 2.6 millimeters, for a length of about 25 centimeters.

This cylindrical tube is in such form that:

it can be connected by spring bias (such as a Lüer cone) to a syringe or to any other device permitting creating an underpressure, at the interior of this tube, is adapted to slide a piston fixed to the distal end of a rod, whilst the other end (proximal) of the rod is secured to a removal member.

As a modification, the tube of the above-mentioned devices can be opened at a first end (proximal end) and comprise at its opposite end (distal end) one or several openings of various shapes, of a diameter most often of about 2 millimeters, a so-called suction hole or distal orifice, and provided on the cylindrical wall of the tube, which is to say in a plane parallel to the longitudinal axis of the tube. Within this latter, is adapted to slide a piston fixed to the distal end of a rod, whilst the other end (proximal) of the rod is secured to a removal member.

The above particularly advantageous devices are characterized in that they are provided, on the side of the distal end of the tube, and adjacent the suction hole, with means permitting improving and increasing the mechanical action for removal of the tube on said wall.

The use, in general a single use, of these known removal devices is as follows:

in the case of removal of physiological liquids, particularly in the case of direct exo or endo-cervical suction, or to carry out for example a Hühner test, after penetration of the uterine neck, the end of the device defined above is introduced into the removal zone: outside the neck or inside the neck, and the aspiration is carried out by pulling on the piston, or by providing vacuum by any suitable means; once the removal is carried out, the device is withdrawn and the removed material is ejected by pressing on the piston;

in the case of removal of mucous fragments, particularly uterine, the device as defined above is introduced through the neck of the patient, into the uterine cavity. Graduations provided on the tube permit locating approximately, by reading these, the position of the distal end of the tube (provided with the distal orifice). The operator, whilst holding the tube by pulling on the rod, by the gripping member, in the direction away from the patient, causes an underpressure within the tube, and hence a suction phenomenon at the orifice disposed at the distal end of the tube. The removal of fragments of the uterine wall and of the uterine mucosa is carried out by moving the tube, preferably by back and forth longitudinal movement, and rotation about the longitudinal axis, whilst holding the distal end of the tube against the wall. Mucosal fragments are thus torn off from the wall and are sucked into the tube through the distal opening or suction hole. This latter, seen from the side, in a plane transverse to the axis of the hole, has a concavity turned outwardly of the tube. In other words, still in a side view, the edges of the hole form a small depression whose concavity is turned outwardly of the tube.

Once the removal operation has been carried out, the operator withdraws the device and then empties the content of the tube resulting from the removal, into a receptacle containing a liquid for histological and/or cytological study.

It will be understood that this type of device must permit removing fragments of the uterine wall (mucosa), in a reliable manner, and of course without pain. Also, the removal must be representative and hence regular, in terms of depth, in a plane transverse to the wall. The removal must also be easy and rapid to speed to the maximum the removal operation, given the discomfort which it holds for the patient.

As to devices for transferring gametes used at present, these latter are intrauterine probes generally comprising a transparent polyethylene probe, of a length of about 17 cm ending in a very flexible catheter with a foam end and having two opposite lateral openings; preferably a normalized connection (such as a Lüer cone) permits the connection of this device to a syringe.

This type of device permits carrying out intrauterine artificial insemination with prepared sperm.

The probe facilitates access to the uterine cavity without trauma and permits freeing the spermatozoa adjacent the tubular ostia. The internal opening of the neck is cleared with the intrauterine probe and the sperm is injected very slowly preferably within 1 cm of the tubular ostia.

As to devices for transferring embryos now used, these latter comprise generally a polyethylene catheter of a length of about 17 to 18.5 cm, having a flexible end of an internal diameter of 1.1 mm, external diameter of 1.6 mm and length of about 4.5 to 5.5 cm, as well as a distal opening.

To carry out the transfer, the above-mentioned catheter is preferably connected to a syringe. The embryos are loaded into the catheter in a very small volume of culture medium, and the catheter must be introduced to within 1 cm of the uterine floor. The embryos are expelled with the help of the syringe.

As a modification, embryo transfer devices comprise:

an introduction catheter, preferably of polypropylene, about 14.5 cm long, with an external diameter of about 2.2 mm, having graduated markings at 1, 2, 3, 4, 5, 6 and 7 cm from its distal end, and being preferably provided with a sliding ring, a reimplantation catheter, preferably of polyurethane, about 23 cm long, with an external diameter of about 1.53 mm and an internal diameter of about 0.7 mm, having graduation marks spaced by one cm in its lower portion, and whose tip is preferably closed by a translucent polyethylene plug.

The use, in general a single use, of this known transfer device is as follows: the introducing catheter is inserted to the internal opening of the neck of the uterus.

Simultaneously, the embryo or embryos have been loaded by the biologician in the reimplantation catheter.

This reimplantation catheter is then introduced into the introducer and will be pressed to the transfer position.

When the first mark of predetermined color of the reimplantation catheter is flush with the proximal end of the Lüer cone of the introducer, their two distal ends coincide. The marks carried by the introducer from its distal end permit computing the length introduced into the uterus. There should be added the excess length of the reimplantation catheter (number of cm by which the concordance marks have been exceeded).

OBJECTS OF THE INVENTION

The present invention has for its object to provide devices for removal or transfer such as defined above, and having the advantage, relative to the existing devices described above, of having an echogenicity and/or radio-opacity which is specifically located at the level of the useful opening of these devices for removing or transfer, and as a result permitting the practitioner to locate even more precisely than is permitted with the devices described above, the zone where this removal or transfer will take place, and no longer to work at random as is the case at present.

The present invention also has for its object to provide devices for removal or transfer as defined above, and having the advantage, relative to the existing devices described above, of being such that the echogenic and/or radio-opaque material is never located outside the removal and/or transfer catheter so as not to impede the introduction of these catheters into the organs in question.

The invention further has for its object providing devices for removal or transfer as defined above, and having the advantage, relative to the existing devices described above, of being such that the echogenic and/or radio-opaque material is never in contact with the removed or transferred products, so as not to alter their physico-chemical characteristics nor their physiological condition.

SUMMARY OF THE INVENTION

The invention relates to all echogenic and/or radio-opaque devices adapted to permit carrying out removals from the genital organs for analysis, such as removal of physiological liquids or fragments of the internal wall of male or female genital organs, more particularly female genital organs, particularly at the level of the neck of the uterus, of the uterus or the anatomical tubes, or adapted to permit the transfer of products such as those selected from gametes, embryos, or active principals, or the products used in radiology in female genital organs, particularly in the female genital organs mentioned above, said device being characterized in that it comprises:
 a catheter for the above-mentioned removal or transfer, to be inserted as the case may be in an introduction catheter serving as a guide, said removal or transfer catheter being of a length greater than that of the introduction catheter, and comprising two parallel channels:
 a first channel (or opening) opens in its distal portion at the level of the orifice used for removal or transfer, and opens at its proximal portion so as to be able to be connected to a suction means such as a syringe,
 a second closed channel in which is disposed an echogenic and/or radio-opaque material at the height of said usable orifice,
 said catheter being as the case may be such that the useful opening of the first channel is closed so as to permit the use of said device in the field of tests for the introduction of catheters into the uterus, and, as the case may be, to learn the morphology of the neck of the uterus and of the uterine cavity, or a catheter for removal comprising a single channel opened in its distal portion at the level of the usable orifice, this latter being adapted to be as the case may be constituted by a lateral opening, even several lateral openings, within which circulates a piston connected to a gripping member (permitting suction of said liquids or physiological fragments), the piston comprising an echogenic and/or radio-opaque material and being located at the height of said usable orifice at the time of introduction of the device into the genital organs, said echogenic and/or radio-opaque material permitting visualizing by medical imagery, particularly by ultrasound or radiography, the positioning of the useful orifice of said device for the removal or the transfer in said organs.

By usable orifice, is meant in the preceding and the following, the hole or holes which, in the above mentioned devices, are those by which the removals are sucked out, or the gametes, embryos, active principals or radiological products are expelled.

Preferably, the echogenic and/or radio-opaque material used in the above-mentioned devices, is selected from:
 substances that can be incorporated in materials of plastic material constituting the device, particularly barium salts, or bismuth salts, or tungsten powder,
 echogenic and/or radio-opaque polymer films, covering all or part of the above-mentioned devices, such as a cladding of polytetrafluoroethylene (PTFE),
 metals, particularly stainless steel based, or gold or copper.

Preferably, in the case of using metals, these can be covered with an echogenic polymer film, particularly PTFE, or even their surface condition can be modified by any suitable technique (for example by depolishing).

The invention relates more particularly to any device as defined above, for removing from the genital organs, said device corresponding to a removal catheter comprising:
 a channel corresponding to a cylindrical tube whose distal end (the farthest from the manipulator) is:
 either open and constitutes the useful orifice for removal of physiological liquids,
 or closed except for at least one so-called suction hole, as the case may be located in a lateral position of the distal end of said catheter, and constituting the usable orifice for the removal of fragments of the walls of genital organs,
 a sealed piston adapted to move in said cylindrical tube, and connected to the distal end of a rod whose proximal end is preferably provided with a gripping member, the distal end of the rod comprising the piston, or the piston itself, comprising an echogenic and radio-opaque material, said material being located at the height of said usable orifice at the time of introduction of the device (piston pressed and held at the height of said orifice) in the neck of the uterus and/or the uterine cavity.

Preferably, the echogenic and/or radio-opaque material used in the removal device described above, is a ring clamped, glued or blocked by overmolding, or any other means, before and/or after and/or in the above-mentioned piston.

The invention also has for its object any device for removal or transfer as defined above, said device corresponding to a catheter comprising:
 a first channel corresponding to a cylindrical tube whose proximal end is adapted to be connected to a syringe permitting suction of the removed materials, or the transfer of the products which it contains, the distal end of this channel being such that it comprises two opposite lateral openings serving as a usable orifice for the transfer, or being open and constituting the usable orifice for the transfer or removal, a second channel corresponding to a cylindrical tube whose proximal and distal ends are closed, and in which is disposed an echogenic and/or radio-opaque material at the height of said usable orifice.

The invention also has for its object any device as defined above, for the practice of test methods for the introduction of catheters into the uterus, and, as the case may be, for analyzing the morphology of the neck and of the uterine cavity, said device corresponding to a catheter comprising:

a first channel corresponding to a cylindrical tube whose proximal end is open or closed, and whose distal end is closed, a second channel corresponding to a cylindrical tube whose proximal and distal ends are closed, and in which is disposed an echogenic and/or radio-opaque material at the height of the distal end.

Preferably, the diameters of the first channel and of the second channel mentioned above in the framework of removal, transfer, or test devices defined above in the scope of the present invention, are respectively about 0.9 to about 1.30 mm, and about 0.4 to about 0.6 mm.

The length of the removal, transfer or test catheters mentioned above is preferably comprised between 150 to about 300 mm.

BRIEF DESCRIPTION OF THE DRAWINGS

The invention will be seen in greater detail with the help of FIGS. 1 to 3, as follows.

Figure 1:
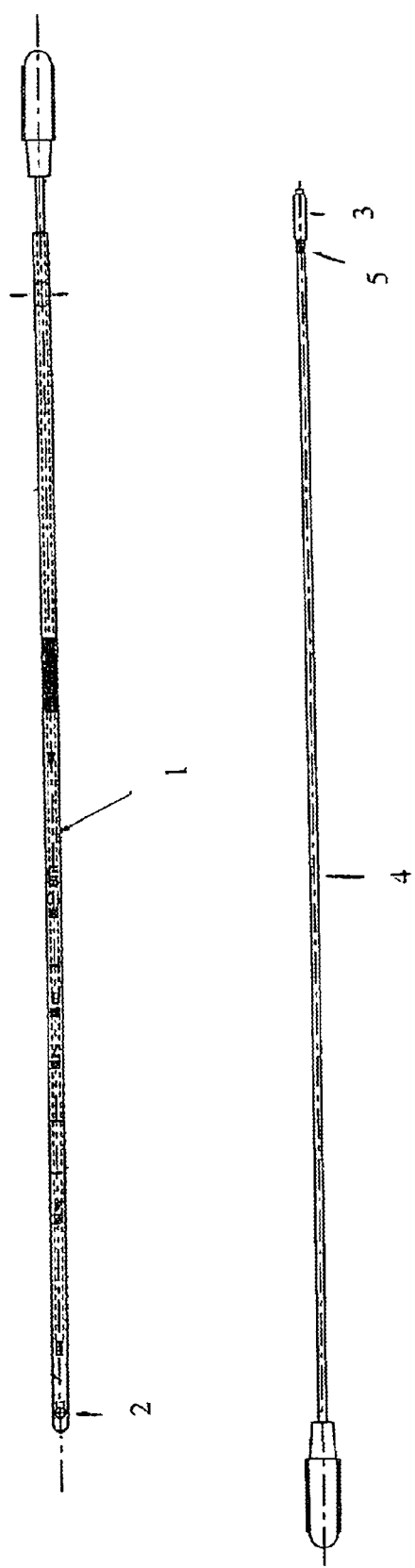
FIG. 1: schematic representation of a removal device according to the invention; the removal catheter is shown at (1), the usable orifice at (2) is here shown in lateral position, the piston at (3), the rod at (4), and the echogenic material at (5).
Figure 2:
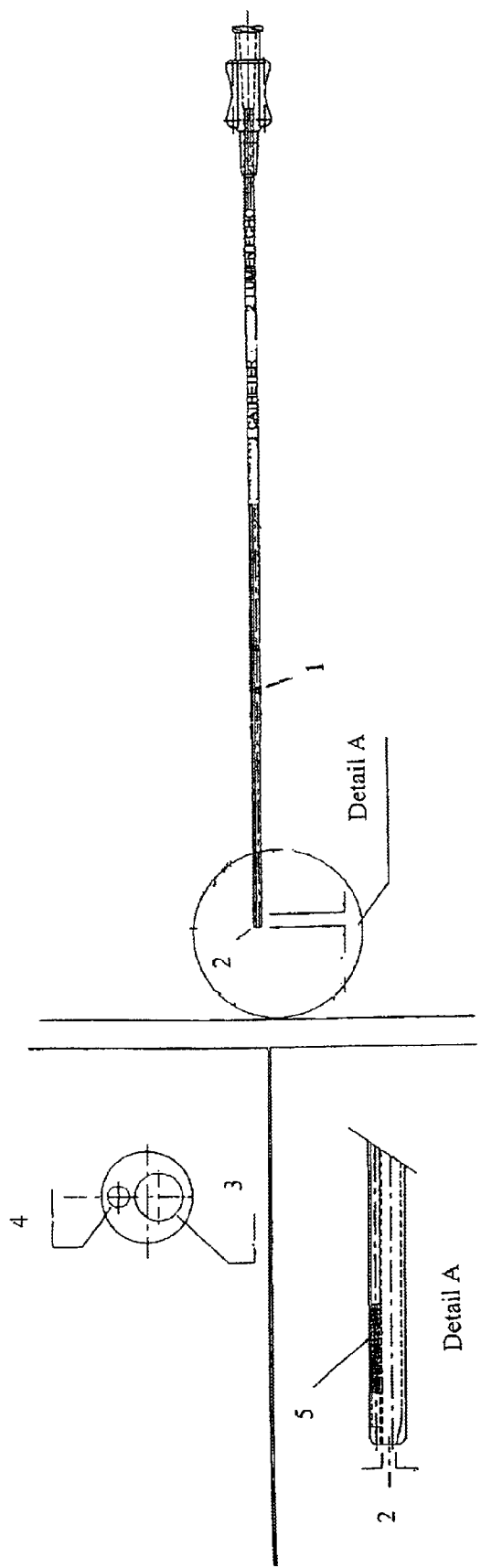
FIG. 2: schematic representation of a removal or transfer device according to the invention; the removal or transfer catheter is shown at (1), the usable opening at (2), the first channel for removal or transfer at (3), the second channel at (4) containing the echogenic material (5); when the usable orifice (2) is closed, there is obtained a test device for studying the morphology of the neck of the uterus or of the uterine cavity.
Figure 3:
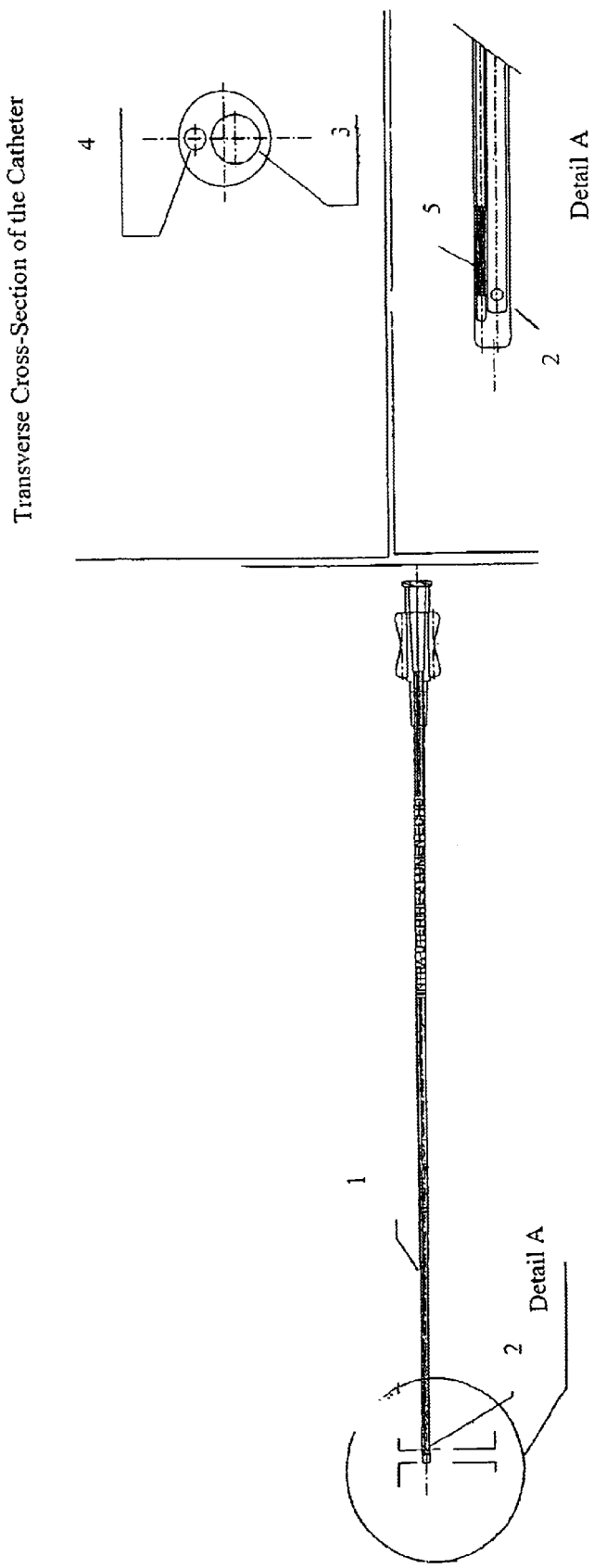
FIG. 3: schematic representation of a transfer device for products according to the invention; the transfer catheter is shown at (1), the usable opening constituted by two opposed openings at (2), the first channel for expulsion of the products at (3), the second channel at (4) containing the echogenic material (5).

What is claimed is:

1. A catheter for the transfer of embryos into female genital organs, comprising:

an elongated member having a first passage therethrough extending from a distal end of said catheter to a proximal end of said catheter, said passage being open at said distal end, and at its proximal end so as to be able to be connected to a syringe, and a second passage parallel to but spaced from said first passage, said second passage closed at both ends and containing an echogenic material wherein the echogenic material is aligned with the open distal end of said first passage along the longitudinal axis of the elongated member, thereby to permit visualizing the position of said open distal end in an area where the transfer should took place.

2. The catheter according to claim 1, wherein said echogenic material is an echogenic polymer film.

3. The catheter according to claim 2, wherein said echogenic polymer film is polytetrafluorethylene.

* * * * *